US006664300B2

(12) United States Patent
Mori et al.

(10) Patent No.: US 6,664,300 B2
(45) Date of Patent: Dec. 16, 2003

(54) PROCESS FOR PRODUCING CAROTENOID EMULSION

(75) Inventors: Toshiki Mori, Niigata (JP); Satoshi Mimura, Niigata (JP); Tomonari Nakatani, Niigata (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/052,456

(22) Filed: Jan. 23, 2002

(65) Prior Publication Data

US 2002/0099102 A1 Jul. 25, 2002

(30) Foreign Application Priority Data

Jan. 24, 2001 (JP) ........................ 2001-015267
Jan. 24, 2001 (JP) ........................ 2001-015274

(51) Int. Cl.[7] ................... A61K 31/015; A23L 1/275; B01F 17/34; B01F 3/08; C12C 5/04
(52) U.S. Cl. ................... 516/73; 426/540; 514/763; 516/77; 516/928
(58) Field of Search ................... 514/763; 426/540; 516/73, 77, 928

(56) References Cited

U.S. PATENT DOCUMENTS

| | | | |
|---|---|---|---|
| 2,861,891 A | | 11/1958 | Bauernfeind et al. |
| 4,522,743 A | * | 6/1985 | Horn et al. ............. 426/540 X |
| 4,726,955 A | * | 2/1988 | Horn et al. ............. 426/540 X |
| 4,844,934 A | * | 7/1989 | Lueddecke et al. ....... 516/73 X |
| 5,364,563 A | | 11/1994 | Cathrein et al. ......... 426/540 X |
| 5,453,447 A | | 9/1995 | End et al. .................... 514/763 |
| 5,925,684 A | * | 7/1999 | Schweikert et al. |
| 6,406,735 B2 | * | 6/2002 | Stein et al. ............. 426/540 X |

FOREIGN PATENT DOCUMENTS

| EP | 0 937 412 | 8/1999 |
|---|---|---|
| JP | 63-196242 | 8/1988 |
| JP | 3-66615 | 3/1991 |
| JP | 6-172170 | 6/1994 |
| JP | 8-119933 | 5/1996 |
| JP | 2000-186224 | 7/2000 |

OTHER PUBLICATIONS

Derwent Abstracts, AN–1994–238646, XP–002196076, JP 06–172170, Jun. 21, 1994.

* cited by examiner

*Primary Examiner*—Richard D. Lovering
(74) *Attorney, Agent, or Firm*—Oblon, Spivak, McClelland, Maier & Neustadt, P.C.

(57) ABSTRACT

A process for producing a carotenoid emulsion which comprises heating a suspension of the carotenoid in a high boiling organic liquid, by passing the suspension through a conduit of 0.1 to 50 mm inside diameter heated to a temperature in the range of 120 to 700° C. for a residence time of 0.05 to 5 seconds or by mixing the suspension with a high boiling organic liquid heated to the range of 120 to 500° C. for a time of 0.05 to 10 seconds, to dissolve the carotenoid, and then immediately adding the resulting solution into an aqueous solution of an emulsifier to emulsify the solution. By this production process, an emulsion containing a carotenoid as an effective ingredient can be produced with the carotenoid maintaining a high total trans-form proportion, with good productivity, conveniently, and industrially advantageously.

34 Claims, 1 Drawing Sheet

PROCESS FOR PRODUCING CAROTENOID EMULSION

BACKGROUND OF THE INVENTION

1. Field of the Invention

This invention relates to a process for producing a carotenoid emulsion.

2. Statement of Related Art

Carotenoids are broadly present in nature, and widely used as colorants for food, etc. utilizing the characteristic that they have yellow to red color. Some carotenoids are also known to show provitamin A activity, cancer-inhibiting effect or the like, and are a compound group drawing attention also from a pharmacological viewpoint. Many isomers are present in carotenoids based on many carbon-carbon double bonds which they possess, and when a use as colorants or a use as a physiologically active agent such as a provitamin A active agent is considered, carotenoids having a high trans-form proportion are preferred.

Carotenoids are compounds which are in a crystalline state at ordinary temperature and have a high melting point, are insoluble in water, extremely low in solubility in organic solvents or fats and oils, and, moreover, tend to be isomerized with heat, and tend to be readily denatured with oxygen or light. Therefore, when it is intended to use carotenoids as colorants for food or a physiologically active agent, they need to be processed into stable and readily utilizable forms. As one process for it, there is a process of producing an emulsion of a carotenoid by mixing the carotenoid into fats and oils and then emulsifying the mixture in an aqueous solution.

Known processes of producing an emulsion of a carotenoid include (1) a process of producing a carotenoid preparation by producing, at 100 to 160° C., a supersaturation solution of a carotenoid in an edible oil which is liquid at about 20 to 40° C. and emulsifying this supersaturation solution into an aqueous gelatin substance (see U.S. Pat. No. 2,861,891), (2) a process of producing a β-carotene preparation having a high trans-form proportion by heating trans-form β-carotene, fats and oils and limonene to make a solution, recovering the limonene and converting the resulting oil layer dissolving the trans-form β-carotene to an emulsion in the presence of an emulsifier (see Japanese Laid-open Patent Publication No. 8-119933), (3) a process of contacting a suspension of a carotenoid in a high boiling oil with superheated steam for maximum 30 seconds and emulsifying the resulting mixture in an aqueous solution of colloid (see Japanese Laid-open Patent Publication No. 3-66615), (4) a process of rapidly dissolving a carotenoid, together with an edible oil of 1.5 to 20 times the mass of the carotenoid and an emulsifier, in a volatile organic solvent miscible with water, at a temperature of 50 to 240° C., then immediately mixing the resulting solution with an aqueous solution of protective colloid at a temperature of 0 to 50° C. to move the hydrophilic solvent components into the aqueous phase and at that time change the hydrophobic oil phase containing and dissolving the carotenoid to a fine dispersion phase (see Japanese Laid-open Patent Publication No. 63-196242), and (5) a process of feeding a suspension of a carotenoid in an organic solvent immiscible with water into a heat exchanger for a residence time of less than 5 seconds to heat the suspension to 100 to 250° C., rapidly mixing the resulting solution with an aqueous solution of easy to swell colloid at a temperature in the range of 20 to 100° C., and then removing the organic solvent (see Japanese Laid-open Patent Publication No. 2000-186224).

DESCRIPTION OF THE INVENTION

Object of the Invention

The process of the above (1) is economically disadvantageous because the visible absorption spectrum of the obtained carotenoid dry powder gets low, and for example in the case of coloring of food, the use quantity of the carotenoid dry powder needs to be increased to obtain a desired value of color strength. The process of the above (2), wherein limonene is used in view of inhibiting isomerization of trans-form β-carotene when the trans-form β-carotene is heated for dissolution, has the problems that the same quantity or more of the limonene as that of the fat or oil needs to be used and further that since limonene is not needed in the final product, a step to remove it is indispensable. The process of the above (3) has the problems that it needs expensive apparatuses because superheated steam being in high temperature and high pressure is used and further that since water originating in the superheated steam, in addition to the water contained in the aqueous solution of colloid, joins the resulting emulsion, when the production of carotenoid powder from the emulsion is intended, a large quantity of water needs to be removed. The processes of the above (4) and (5) have the problems that since the used organic solvent is unnecessary for the final product, it needs to be removed and that use of a large quantity of the organic solvent is needed, which lowers productivity. Therefore, it is hard to say that any of these processes are industrially advantageous production process.

Thus, the object of the invention lies in providing a process capable of producing an emulsion containing a carotenoid as an effective ingredient with the carotenoid maintaining a high total trans-form proportion, with good productivity, conveniently, and industrially advantageously.

SUMMARY OF THE INVENTION

The present inventors have made intense researches for accomplishing the above object. As a result, we found that, in steps of producing a carotenoid emulsion, by using a process of passing a suspension of a carotenoid in a high boiling organic liquid, in a short time, through a conduit having a particular pipe diameter heated to a temperature in a particular range, or a process of mixing the suspension, in a short time, with a high boiling organic liquid (preferably the same kind of a high boiling organic liquid as used in preparation of the suspension) heated to a particular temperature range, it is possible to give a large quantity of heat to the suspension in a short time and dissolve the carotenoid in the high boiling organic liquid with inhibition of isomerization of the carotenoid, and by using a process of immediately emulsifying the resulting solution, it is possible to produce a carotenoid emulsion not containing any organic solvent and a large quantity of water unnecessary for final products. We further found that carotenoid powder obtained by spray drying a carotenoid emulsion obtained by such a process or by stirring the carotenoid emulsion in a nonpolar solvent to make the emulsion particles, and filtering and drying the particles can be used as colorants for food or a physiologically active agent, and completed the invention.

Namely, the present invention relates to

① a process for producing a carotenoid emulsion which comprises heating a suspension of the carotenoid in a high boiling organic liquid (hereinafter, sometimes merely abbreviated as "carotenoid suspension" ), by passing the suspension through a conduit of 0.1 to 50 mm inside diameter heated to temperature in the range of 120 to 700°

C. for a residence time of 0.05 to 5 seconds or by mixing the suspension with a high boiling organic liquid heated to the range of 120 to 500° C. for a time of 0.05 to 10 seconds, to dissolve the carotenoid, and then immediately adding the resulting solution into an aqueous solution of an emulsifier to emulsify the solution, and (2) carotenoid powder obtained by spray drying the resulting carotenoid emulsion or by stirring the carotenoid emulsion in a nonpolar solvent to make the emulsion particles, and filtering and drying the particles.

BRIEF DESCRIPTION OF THE DRAWINGS

In FIG. 1 the symbols have the following meanings, respectively.

1 Tank
2 Metering pump
3 Vessel containing a heat medium
4 Conduit
5 Change-over device
6 Emulsifier
7 Vessel (an aqueous solution of an emulsifier is charged)
8 Receiver
9 Heating apparatus
In FIG. 2 the symbols have the following meanings, respectively.

Figure 1:
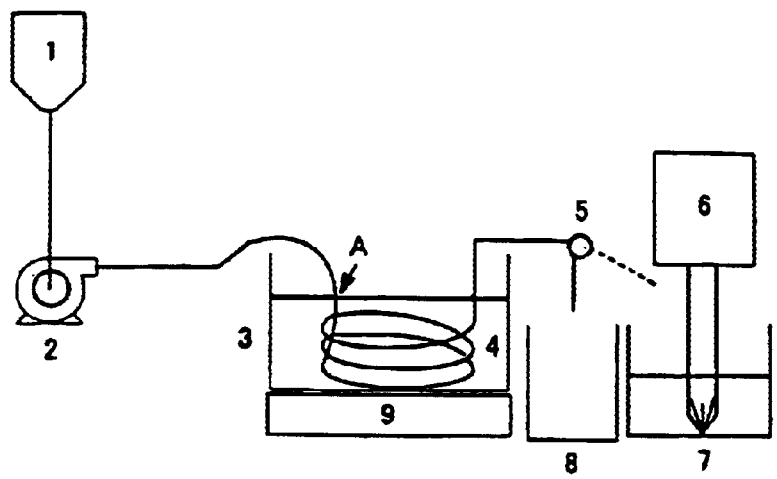
FIG. 1 shows an embodiment of the production process of the invention.

11, 16 Tank
12, 17 Metering pump
13 Vessel containing a heat medium
14 Heating apparatus
15, 18, 19 Conduit
20 Change-over device
21 Emulsifier
22 Vessel (an aqueous solution of an emulsifier is charged)
23 Receiver
K Cock

DESCRIPTION OF PREFERRED EMBODIMENTS

As carotenoids used in the invention, there can be exemplified β-carotene, canthaxanthin, astaxanthin, apocarotenal, citranaxanthin, cryptoxanthin, etc. As to the size of crystals of carotenoids, in view of smoothly carrying out the dissolution of the carotenoid in the high boiling organic liquid by heating a suspension of a carotenoid in a high boiling organic liquid, it is preferred to use the crystals having a particle size of 50 μm or less and it is further preferred to use the crystals having a particle size of 15 μm or less.

In the scope of the specification, the term "high boiling organic liquid" includes paraffins having 10 to 40 carbon atoms; terpene compounds having 10 to 50 carbon atoms such as myrcene, terpine oil and squalane; fatty acid glycerides having 10 to 80 carbon atoms, and particularly meant are fatty acid glycerides having 10 to 80 carbon atoms. As such fatty acid glycerides, there can, for example, be mentioned fatty acid triglycerides such as glyceryl tricaprylate, glyceryl trilaurate, glyceryl trimyristate, glyceryl tripalmitate, glyceryl tristearate, glyceryl trioleate, glyceryl trilinolate and glyceryl trilinolenate, fatty acid diglycerides which are in such a form that one fatty acid is removed from fatty acid triglycerides, such as glyceryl dicaprylate, glyceryl dilaurate, glyceryl dimyristate, glyceryl dipalmitate, glyceryl distearate, glyceryl dioleate, glyceryl dilinolate and glyceryl dilinolenate, and further fatty acid monoglycerides which are in such a form that two fatty acids are removed from fatty acid triglycerides, such as glyceryl monocaprylate, glyceryl monolaurate, glyceryl monomyristate, glyceryl monopalmitate, glyceryl monostearate, glyceryl monooleate, glyceryl monolinolate and glyceryl monolinolenate. These fatty acid glycerides can be used alone or in combination of two or more, and it is of course possible to use edible oils, each of which is a mixture of fatty acid glycerides, such as soybean oil, corn oil, peanut oil, coconut oil, sesame oil, sunflower seed oil and cotton seed oil generally in circulation. Mixtures of fatty acid triglycerides, fatty acid diglycerides and fatty acid monoglycerides in arbitrary proportions are also included in the high boiling organic liquid in the invention.

Such high boiling organic liquids generally have a boiling point of 150° C. or more at ordinary pressure, and act as a solvent/carrier substance for carotenoids used in the invention.

Carotenoids are sensitive to oxygen, and therefore it is preferred to add an antioxidant to the high boiling organic liquid in preparation of a carotenoid suspension. As the antioxidant, there can, for example, be mentioned t-butylhydroxyanisole, t-butylhydroxytoluene, vitamin E, etc., and vitamin E is particularly preferred. These antioxidants can be mixed with the high boiling organic liquid at any proportion and used, but it is, usually, preferred to use such an antioxidant in the range of 0 to 10 times the mass of the used carotenoid.

There is no particular limitation on the proportion of the carotenoid to the high boiling organic liquid in preparation of a carotenoid suspension, but, usually, it is preferred that the content of carotenoid in the whole suspension is in the range of 0.5 to 90% by mass, and it is further preferred that the content is in the range of 1 to 40% by mass.

According to the invention, first, a suspension of a carotenoid in a high boiling organic liquid is heated to dissolve the carotenoid. There are two processes for this dissolution by heating, and one is a process of heating the suspension in a short time by passing the suspension through a heated conduit to dissolve the carotenoid, and the other is a process of heating the suspension in a short time by mixing the suspension with a heated high boiling organic liquid to dissolve the carotenoid.

In the former heating process, the heating temperature of the conduit may vary depending on the kinds of the carotenoid and high boiling organic liquid constituting the suspension to be passed, the use proportion of the carotenoid to the high boiling organic liquid, the passing quantity and passing rate of the suspension, etc., but the heating temperature is necessarily in the range of 120 to 700° C., preferably in the range of 120 to 600° C., more preferably in the range of 130 to 500° C. When the heating temperature of the conduit is lower than 120° C., dissolution of the carotenoid in the carotenoid suspension is not sufficiently made and undissolved carotenoid crystals remain, and due to these remaining crystals, dispersibility of carotenoid in a finally obtained carotenoid emulsion is lowered. Further, when the heating temperature of the conduit is higher than 700° C., the carotenoid itself is deteriorated by the heat.

As means for heating the conduit, ordinal heating means can be adopted such as a method to use a gas burner, an electric heater, electromagnetic induction or the like, a method to heat the conduit by using an organic heating medium such as a usual heating medium oil or an inorganic heating medium such as HTS (Heat Transfer Salt: mixture of sodium nitrite, sodium nitrate and potassium nitrate).

Before passing it through the heated conduit, the carotenoid suspension can previously be heated at such a temperature that the carotenoid is not isomerized. When the carotenoid suspension is previously heated, the heating temperature is, usually, preferably in the range of 40 to 140° C., and more preferably in the range of 60 to 120° C.

The material of the conduit is not particularly limited so long as it is usable in the process of the invention, and includes, for example metals such as iron, stainless steel and titanium, glasses, etc. As to the shape of the conduit, any shape can be adopted, and example thereof are linear conduits, conduits of a coil shape, etc. Further, in view of further improving the productivity, it is also possible to use plural conduits with parallel connection.

In the process of the invention, the inside diameter of the conduit to be used is necessarily in the range of 0.1 to 50 mm, and preferably in the range of 0.5 to 10 mm. When such a thin conduit that the inside diameter of the conduit is less than 0.1 mm is used, clogging is liable to occur in the conduit when the carotenoid suspension is passed, and on the other hand, when a conduit having an inside diameter of more than 50 mm, it gets very hard to heat the carotenoid suspension, in a short time, to such a temperature that the carotenoid dissolves in the high boiling organic liquid.

As to the thickness of the conduit, there is no particular limitation, but in view of efficiently supplying quantity of heat to the carotenoid suspension and in view of withstanding the pressure given to the conduit when the suspension is passed, the thickness of the conduit is, usually, preferably on the order of 1/10 to 10 times the inside diameter of the conduit, more preferably on the order of 1/5 to 5 times the inside diameter.

The length of the conduit of the part heated in the range of 120 to 700° C. may vary depending on the kinds of the carotenoid and the high boiling organic liquid constituting the carotenoid suspension to be passed, the use proportion of the carotenoid to the high boiling organic liquid, and the passing quantity and passing rate of the suspension, but in view of supplying enough heat quantity to dissolve the carotenoid in the high boiling organic liquid and in view of inhibiting the isomerization of the carotenoid with heat as completely as possible, while passing the carotenoid suspension through the conduit, the length of the conduit of the part is, usually, preferably in the range of 0.3 to 20 m, more preferably in the range of 0.5 to 10 m.

When the carotenoid suspension is passed through the heated conduit, time when the suspension resides in the heated conduit is necessarily in the range of 0.05 to 5 seconds, preferably 0.1 to 3 seconds, in view of inhibiting the isomerization of the carotenoid with heat as completely as possible.

As means for transferring the carotenoid suspension to the conduit of the part heated in the range of 120 to 700° C., means usually used when liquid is transferred, such as metering pumps and compressed gases, can be used. The amount of the carotenoid suspension to be transferred may vary depending on the kinds of the carotenoid and the high boiling organic liquid constituting the suspension to be passed, the use proportion of the carotenoid to the high boiling organic liquid, the heating temperature of the conduit, and time when the suspension is made to reside in the heated conduit, but the quantity is, usually, preferably in the range of 0.05 to 100 liters/minute, more preferably in the range of 0.1 to 20 liters/minute. When the carotenoid suspension is passed through the conduit at a flow rate of the above range, pressure at the time of liquid transfer is usually in the range of 0.001 to 20.2 MPa (0.01 to 200 kg/cm$^2$) as gage pressure.

There is no particular limitation on the size and length of the conduit up to introduction of the carotenoid suspension into the inlet of the heated conduit part. On the other hand, as to the size and length of the conduit from the outlet of the heated conduit part to the emulsifier, the length of the conduit is preferably as short as possible in view of inhibiting the isomerization of the carotenoid with heat, and is, usually, preferably in the range of 0.01 to 2 m.

Advantageously, it is, for example, possible to make the conduit from the tank charged with the carotenoid suspension to the introduction part of the heated conduit, the heated conduit and the conduit from the heated conduit to the emulsifier using tubes of the same material and the same diameter.

Description is made now on the second process for heating a suspension of a carotenoid in a high boiling organic liquid to dissolve the carotenoid, namely the process of mixing the suspension with a heated high boiling organic liquid to dissolve the carotenoid. The heated high boiling organic liquid to be mixed with the carotenoid suspension may be the same or different kind of high boiling organic liquid as used in preparation of the suspension, but it is preferred to use the same kind of high boiling organic liquid as in preparation of the suspension.

The heating temperature of the heated high boiling organic liquid to be mixed with the carotenoid suspension is necessarily in the range of 120 to 500° C., preferably in the range of 150 to 500° C., more preferably in the range of 180 to 450° C. When the temperature is less than 120° C., it is impossible to supply enough heat quantity to dissolve the carotenoid in the high boiling organic liquid, and on the other hand, when the temperature is more than 500° C., in mixing of both the quantity of the carotenoid isomerized with heat increases.

The amount of the heated high boiling organic liquid to be mixed with the carotenoid suspension is not strictly limited, and may vary depending on the content of the carotenoid in the carotenoid suspension, the heating temperature of the heated high boiling organic liquid, etc., but taking a practical range of the carotenoid content in the resulting carotenoid emulsion and a range capable of surely dissolving the carotenoid by the mixing into account, the amount of the high boiling organic liquid as the total of the quantity of the heated high boiling organic liquid and the quantity of the high boiling organic liquid constituting the carotenoid suspension is, usually, preferably in the range of 1 to 20 times, more preferably in the range of 2 to 10 times the mass of the carotenoid contained in the carotenoid suspension.

As means for the preparation of the heated high boiling organic liquid to be mixed with the carotenoid suspension, there can be adopted usual heating means, for example a method using a gas burner, an electric heater, electromagnetic induction or the like, a method of carrying out heating by using an organic heating medium such as a usual heating medium oil or an inorganic heating medium such as HTS (Heat Tranfer Salt: mixture of sodium nitrite, sodium nitrate and potassium nitrate).

Before mixing the carotenoid suspension with the heated high boiling organic liquid, the suspension can previously be heated at such a temperature that the carotenoid is not isomerized. When the carotenoid suspension is previously heated, the heating temperature is, usually, preferably in the range of 40 to 140° C., more preferably in the range of 60 to 120° C.

Time for mixing the carotenoid suspension with the heated high boiling organic liquid is important, and time from the moment when both contact (time of starting the mixing) to the addition for emulsification of the resulting solution of the carotenoid in the high boiling organic liquid into an aqueous solution of an emulsifier described later is necessarily in the range of 0.05 to 10 seconds, preferably in the range of 0.05 to 5 seconds. When the time for mixing the carotenoid suspension with the heated high boiling organic liquid is shorter than 0.05 second, it is impossible to supply enough heat quantity to dissolve the carotenoid in the high boiling organic liquid, and on the other hand when the time is longer than 10 seconds, deterioration and isomerization of the carotenoid with heat become actual.

Means for mixing the carotenoid suspension with the heated high boiling organic liquid are not particularly limited, but preferred, in view of immediately adding the solution of the carotenoid in the high boiling organic liquid obtained by the mixing to an aqueous solution of an emulsifier to carry out emulsification, are, for example a method of feeding both into the same conduit to mix them, a method of feeding both into a tube having a mixing function such as a line mixer to mixing them, a method of continuously feeding both into a vessel having a stirring device and making them reside within the above mixing time to continuously mix them, etc.

As mentioned above, by passing a suspension of a carotenoid in a high boiling organic liquid through a heated conduit or by mixing the suspension with a heated high boiling organic liquid, a solution of the carotenoid in the high boiling organic liquid can be prepared, and the solution is then immediately subjected to a step of adding the solution to an aqueous solution of an emulsifier to emulsify the former solution.

As to the emulsifier, there is no particular limitation so long as it is capable of emulsifying the high boiling organic liquid and water, and there can, for example, be mentioned fatty acid esters of ascorbic acid such as ascorbic acid palmitate and ascorbic acid monooleate, sucrose fatty acid esters such as sucrose palmitate and sucrose monooleate, sorbitan fatty acid esters such as sorbitan palmitate and sorbitan monooleate, etc. Among them, it is particularly preferred to use fatty acid esters of ascorbic acid such as ascorbic acid palmitate. The emulsifier is used as a solution in water, and when a fatty acid ester of ascorbic acid is used, an alkali metal compound such as sodium hydroxide or sodium carbonate may additionally be added in dissolution thereof.

In view of improving the stability of the produced carotenoid emulsion, gelatin, sugars, gum arabic, starches or the like may additionally be added to the aqueous solution of the emulsifier.

There is no particular limitation on the ratio in use quantity between the emulsifier and the water constituting the aqueous solution of the emulsifier. The amount of the aqueous solution of the emulsifier is not particularly limited so long as it is an enough quantity to emulsify the high boiling organic liquid containing carotenoid, namely an enough quantity to form a stable O/W emulsion, but, usually, it is preferred that the amount of the aqueous solution of the emulsifier is such that the quantity of the emulsifier is 0.1 to 2 times the mass of the solution of the carotenoid in the high boiling organic liquid and the quantity of the water is 0.1 to 1,000 times the mass of the solution.

At the time of emulsifying the solution of the carotenoid in the high boiling organic liquid by adding it to the aqueous solution of the emulsifier, the temperature of the mixture of both is preferably maintained at 90° C. or less, more preferably in the range of 0 to 90° C., and particularly preferably in the range of 20 to 80° C. When the temperature of the mixture is higher than 90° C., the water gets close to a boiled state, and on the other hand when it is lower than 0° C., the water gets close to a frozen state, and in both cases, since the formation of a stable emulsion is prevented, a good carotenoid emulsion cannot be obtained.

The step of adding the solution of the carotenoid in the high boiling organic liquid to the aqueous solution of the emulsifier to emulsify the solution can, for example, be carried out by previously charging an aqueous solution of an emulsifier in a vessel equipped with a stirring-type emulsifier and intermittently or continuously adding the solution of the carotenoid in the high boiling organic liquid to carry out emulsification. It is also possible to carry out the emulsification by introducing the solution of the carotenoid in the high boiling organic liquid and the aqueous solution of the emulsifier together into a line mixer.

The process of the invention is a series of operations from an operation of heating a suspension of a carotenoid in a high boiling organic liquid by passing the suspension through a heated conduit or by mixing the suspension with a heated high boiling organic liquid, to dissolve the carotenoid, to an operation of adding the resulting solution of the carotenoid in the high boiling organic liquid to an aqueous solution of an emulsifier to emulsify the solution, and a carotenoid emulsion can be obtained by such convenient operations. The process of the invention can be carried out by either of a batch type and a continuous type.

The obtained carotenoid emulsion can be used as it is for a use as colorants for food or a feed additive. Further, by spray drying the carotenoid emulsion, or by stirring the carotenoid emulsion in a nonpolar solvent such as hexane, toluene or a paraffin to make the emulsion particles, and filtering and drying the particles, powder containing the carotenoid can be obtained.

EXAMPLES

The present invention will now be described in detail below through examples, but the present invention is not limited at all by these examples.

An embodiment of the production process of the present invention is shown in FIG. 1. A suspension of a carotenoid in a high boiling organic liquid is charged into Tank 1. The carotenoid suspension is fed from Tank 1 into Conduit 4 immersed in a heating medium in Vessel 3 heated by Heating apparatus 9, via Metering pump 2, and thereby the suspension becomes, in the heated Conduit 4, such a solution that the carotenoid is dissolved in the high boiling organic liquid. This solution is immediately intermittently or continuously fed into Vessel 7 in which an aqueous solution of an emulsifier is previously charged, Vessel 7 being equipped with Emulsifier 6. 5 is a change-over device for feeding the solution of the carotenoid in the high boiling organic liquid into Vessel 7 or Receiver 8.

Figure 2:
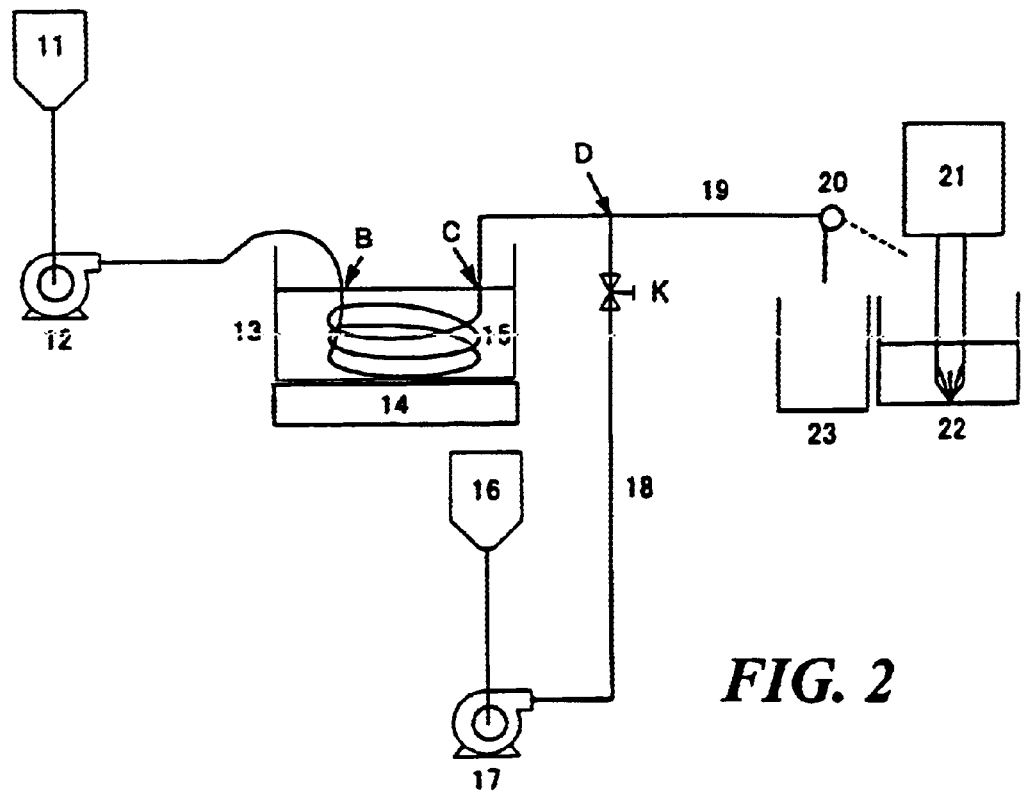
FIG. 2 shows an embodiment of the production process of the invention.

Another embodiment of the production process of the invention is shown in FIG. 2. A high boiling organic liquid is put in Tank 11, and the carotenoid suspension is charged in Tank 16. The high boiling organic liquid is transferred from Tank 11 to Conduit 15 immersed in Vessel 13 containing a heating medium via Quantitative liquid-transferring pump 12. On the other hand, the carotenoid suspension which is transferred from Tank 16 via Metering pump 17 and Conduit 18 joins the heated high boiling organic liquid described above at Point D. Both are mixed in Conduit 19 and become a solution of such a state that the carotenoid is dissolved in the high boiling organic liquid, and the solution is intermittently or continuously fed into Vessel 22 in which an aqueous solution of an emulsifier was previously charged, Vessel 22 being equipped with Emulsifier 21. 20 is a change-over device for feeding the solution of such a state that the carotenoid is dissolved in the high boiling organic liquid into Vessel 22 or Receiver 23, and K is a cock.

Example 1

Production of β-Carotene Emulsion

In FIG. 1, as Conduit 4 was used such a loose coil-shaped stainless steel conduit that the inside diameter is 2 mm, the outside diameter is 3 mm and the length from Point A immersed in the heating medium to Change-over device 5 equipped with two nozzles each 5 cm long is 2.5 m. This Conduit 4 was put in Vessel 3 (the length of the part immersed in the heating medium: 2.2 m) and heated to 344° C.

A solution prepared by dissolving 3.0 g of ascorbic acid palmitate, 9 g of aqueous one normal (1 N) sodium hydroxide solution, 4 g of gelatin and 4 g of sugar in 200 g of water was put in Vessel 7 (capacity: 500 ml), heated to 50° C., and stirred at 17,000 revolutions/minute using Emulsifier 6 (clear mixer emulsifier). A suspension prepared by suspending 300 g of β-carotene (purity 98%, total trans-form proportion 99%) in 1,100 g of corn oil and 100 g of monoolein was put in Tank 1, and Tank 1 was heated to 80° C. Change-over device 5 was set at the side of Receiver 8, transfer of the β-carotene suspension in Tank 1 at a flow rate of 1.68 liters/minute was started by Metering pump 2, and when the flow rate gets constant, Change-over device 5 was changed over to the side of Vessel 7 for 2.5 seconds to introduce the solution of β-carotene. At this time, the liquid-transferring pressure of Metering pump 2 was 3.43 MPa (34 kg/cm$^2$) as gage pressure and the temperature of the solution at the time of passing through Change-over device 5 was 160° C. Then, Change-over device 5 was brought back again to the side of Receiver 8 and Metering pump 2 was stopped. After the introduction of the solution of β-carotene, emulsification operation in Vessel 7 was made for 6 minutes to obtain a β-carotene emulsion. The temperature of the mixture in Vessel 7 immediately after the introduction of the solution of β-carotene was 55° C., and the temperature of the emulsion in Vessel 7 after the emulsification operation was made for 6 minutes was 60° C. When the resulting emulsion was analyzed, this emulsion contained 4.2% of β-carotene and its total trans-form proportion was 98%.

Example 2

Production of Canthaxanthin Emulsion

The same apparatus as in Example 1 was used, and Conduit 4 was heated to 342° C. A solution prepared by dissolving 3.0 g of ascorbic acid palmitate, 9.0 g of aqueous one normal (1 N) sodium hydroxide solution, 4 g of gelatin and 4 g of sugar in 200 g of water was put in Vessel 7 (capacity: 500 ml), heated to 50° C., and stirred at 17,000 revolutions/minute using Emulsifier 6 (clear mixer emulsifier). A suspension prepared by suspending 300 g of canthaxanthin (purity 96%, total trans-form proportion 97%) in 1,100 g of corn oil and 100 g of monoolein was put in Tank 1, and Tank 1 was heated to 80° C. Change-over device 5 was set at the side of Receiver 8, transfer of the canthaxanthin suspension in Tank 1 at a flow rate of 1.44 liters/minute was started by Metering pump 2, and when the flow rate gets constant, Change-over device 5 was changed over to the side of Vessel 7 for 2 seconds to introduce the canthaxanthin solution. At this time, the liquid-transferring pressure of Metering pump 2 was 3.03 MPa (30 kg/cm$^2$) as gage pressure and the temperature of the solution at the time of passing through Change-over device 5 was 167° C. Then, Change-over device 5 was brought back again to the side of Receiver 8 and Metering pump 2 was stopped. After the introduction of the solution of canthaxanthin, emulsification operation in Vessel 7 was made for 6 minutes to obtain a canthaxanthin emulsion. The temperature of the mixture in Vessel 7 immediately after the introduction of the solution of canthaxanthin was 56° C., and the temperature of the emulsion in Vessel 7 after the emulsification operation was made for 6 minutes was 61° C. When the resulting emulsion was analyzed, this emulsion contained 3.0% of canthaxanthin and its total trans-form proportion was 62%.

Example 3

Production of β-Carotene Emulsion

In FIG. 2, as Conduit 15 was used such a stainless steel conduit that the inside diameter was 2 mm, the outside diameter was 3 mm, the length from Point B to Point C immersed in the heating medium was 2.2 m, the part from Point B to Point C has a loose coil shape, and the length from Point C to Point D was 0.2 m. This Conduit 15 was heated with the heating medium heated to 387° C. in Vessel 13. As Conduit 18 was used such a stainless steel conduit that the inside diameter was 6 mm, the outside diameter was 8 mm, the length from Metering pump 17 to Point D was 0.6 m, and Cock K was installed at the position of 0.1 m from Point D. As Conduit 19 was used such a stainless steel conduit that the inside diameter was 3 mm, the outside diameter was 4 mm and the length from Point D to Change-over device 20 was 1.5 m.

A solution prepared by dissolving 3.0 g of ascorbic acid palmitate, 9.0 g of aqueous one normal (1 N) sodium hydroxide solution, 4 g of gelatin and 4 g of sugar in 200 g of water was put in Vessel 22 (capacity: 500 ml), heated to 50° C., and stirred at 17,000 revolutions/minute using Emulsifier 21 (clear mixer emulsifier).

Corn oil was put in Tank 11. A suspension prepared by suspending 300 g of β-carotene (purity 98%, total transform proportion 99%) in 1,100 g of corn oil and 100 g of monoolein was put in Tank 16 and heated to 80° C. Cock K was turned off, Change-over device 20 was set at the side of Receiver 23, transfer of the corn oil in Tank 11 at a flow rate of 1.7 liters/minute was started by Metering pump 12, and it was confirmed at the position of Change-over device 20 that the temperature of the corn oil discharged at the outlet of the nozzle (length 5 cm) was 190° C. Then, Metering pump 17 was put into operation at a flow rate of 0.8 liter/minute and a liquid-transferring pressure of 1.21 MPa (12 kg/cm$^2$) as gage pressure, and at the same time, Cock K was tuned on. After confirming that a red solution showing that β-carotene was in a dissolved state was started to be discharged from the nozzle of Change-over device 20, Change-over device 20 was changed over to the side of Vessel 22 for 2 seconds to introduce the solution wherein the β-carotene was in a dissolved state. At this time, the temperature of the discharged solution at the outlet of the nozzle was 149° C.

Then, Change-over device 20 was brought back again to the side of Receiver 23 and Metering pumps 12 and 17 were stopped. After the introduction of the solution wherein the β-carotene was in a dissolved state, emulsification operation in Vessel 22 was made for 6 minutes to obtain a β-carotene emulsion. The temperature of the mixture in Vessel 22 immediately after the introduction of the solution wherein the β-carotene was in a dissolved state was 53° C., and the temperature of the emulsion in Vessel 22 after the emulsification operation was made for 6 minutes was 58° C. When the resulting emulsion was analyzed, this emulsion contained 1.7% of β-carotene and its total trans-form proportion was 98.5%.

Example 4

Production of Canthaxanthin Emulsion

The same apparatus as in Example 3 was used, and the heating medium in Vessel 13 was heated to 410° C.

A solution prepared by dissolving 3.0 g of ascorbic acid palmitate, 9.0 g of aqueous one normal (1 N) sodium hydroxide solution, 4 g of gelatin and 4 g of sugar in 200 g of water was put in Vessel 22 (capacity: 500 ml), heated to 50° C., and stirred at 17,000 revolutions/minute using Emulsifier 21 (clear mixer emulsifier).

Corn oil was put in Tank 11. A suspension prepared by suspending 300 g of canthaxanthin (purity 97%, total trans-form proportion 96%) in 1,100 g of corn oil and 100 g of monoolein was put in Tank 16 and heated to 80° C. Cock K was turned off, Change-over device 20 was set at the side of Receiver 23, transfer of the corn oil in Tank 11 at a flow rate of 1.7 liters/minute was started by Metering pump 12, and it was confirmed at the position of Change-over device 20 that the temperature of the corn oil discharged at the outlet of the nozzle was 193° C. Then, Metering pump 17 was put into operation at a flow rate of 0.26 liter/minute and a liquid-transferring pressure of 1.21 MPa (12 kg/cm$^2$) as gage pressure, and at the same time, Cock K was tuned on. After confirming that a red solution showing that canthaxanthin was in a dissolved state was started to be discharged from the nozzle of Change-over device 20, Change-over device 20 was changed over to the side of Vessel 22 for 2 seconds to introduce the solution wherein the canthaxanthin was in a dissolved state. At this time, the temperature of the discharged solution at the outlet of the nozzle was 178° C. Then, Change-over device 20 was brought back again to the side of Receiver 23 and Metering pumps 12 and 17 were stopped. After the introduction of the solution wherein the canthaxanthin was in a dissolved state, emulsification operation in Vessel 22 was made for 6 minutes to obtain a canthaxanthin emulsion. The temperature of the mixture in Vessel 22 immediately after the introduction of the solution wherein the canthaxanthin was in a dissolved state was 57° C., and the temperature of the emulsion in Vessel 22 after the emulsification operation was made for 6 minutes was 63° C. When the resulting emulsion was analyzed, this emulsion contained 0.61% of canthaxanthin and its total trans-form proportion was 69.5%.

Comparative Example 1

A mixture of 20 g of corn oil, 4 g of monoolein and 2 g of vitamin E was put in an egg-plant type flask (capacity: 50 ml) and heated to 100° C. by a mantle heater. Then, 12 g of carotene crystals (purity 97.8%, total trans-form proportion 98.4%) were added thereto and the mixture was heated for 2 minutes. The resulting solution was put all at once in a beaker (capacity: 300 ml) containing 2 g of gelatin, 2 g of sugar, 1.5 g of ascorbic acid palmitate, 4.5 g of aqueous one normal (1 N) sodium hydroxide solution and 100 g of water, and the mixture was stirred at 60° C. and at 17,000 revolutions/minute for 6 minutes using an emulsifier (clear mixer emulsifier). When the resulting emulsion was analyzed, this emulsion contained 5.0% of β-carotene and its total trans-form proportion was 65%.

As shown in the above, according to the present invention, an emulsion containing a carotenoid as an effective ingredient can be produced with the carotenoid maintaining a high total trans-form proportion, with good productivity, conveniently, and industrially advantageously.

We claim:

1. A process for producing a carotenoid emulsion which comprises heating a suspension of the carotenoid in a high boiling organic liquid having a boiling point of at least 150° C. (hereinafter referred to as carotenoid suspension), by passing the suspension through a conduit of from 0.1 to 50 mm inside diameter heated to a temperature in the range of from 120 to 700° C. for a residence time of 0.05 to 5 seconds or by mixing the suspension with a high boiling organic liquid having a bailing point of at least 150° C. heated to a temperature in the range of 120 to 500° C. for a time of from 0.05 to 10 seconds, to dissolve the carotenoid, and then immediately adding the resulting solution into an aqueous solution of an emulsifier to emulsify the solution, wherein the carotenoid suspension is heated at such a temperature that the carotenoid is not isomerized before it is heated to dissolve the carotenoid.

2. The process according to claim 1, wherein the carotenoid is at least one selected from the group consisting of β-carotene, canthaxanthin, astaxanthin, apocarotenal, citranaxanthin and cryptoxanthin.

3. The process according to claim 1, wherein the particle size of the carotenoid is 50 μm or less.

4. The process according to claim 1, wherein the high boiling organic liquid is a paraffin having 10 to 40 carbon atoms, a terpene compound having 10 to 50 carbon atoms or a fatty acid glyceride having 10 to 80 carbon atoms.

5. The process according to claim 1, wherein the high boiling organic liquid is at least one selected from the group consisting of a fatty acid triglyceride, a fatty acid diglyceride, a fatty acid monoglyceride and an edible oil.

6. The process according to claim 1, wherein an antioxidant is added in preparation of the carotenoid suspension.

7. The process according to claim 1, wherein the content of carotenoid in the carotenoid suspension is 0.5 to 90% by mass based on the whole carotenoid suspension.

8. The process according to claim 1, wherein the emulsifier is a fatty acid ester of ascorbic acid, a sucrose fatty acid ester or a sorbitan fatty acid ester.

9. The process according to claim 1, wherein the temperature at the time of the emulsification is 90° C. or less.

10. A process for producing a carotenoid emulsion which comprises heating a suspension of the carotenoid in a high boiling organic liquid having a boiling point of at least 150° C., by passing the suspension through a conduit of from 0.1 to 50 mm inside diameter heated to a temperature in the range of from 120 to 700° C. for a residence time of 0.05 to 5 seconds or by mixing the suspension with a high boiling organic liquid having a boiling point of at least 150° C. heated to a temperature in the range of 120 to 500° C. for a time of from 0.05 to 10 seconds, to dissolve the carotenoid, and then immediately adding the resulting solution into an aqueous solution of an emulsifier to emulsify the solution, wherein the dissolution of carotenoid by heating is carried out by passing the carotenoid suspension through the heated conduit and the length of the conduit of the part heated to a temperature in the range of 120 to 700° C. is 0.3 to 20 m.

11. The process according to claim 10, wherein the temperature of heating of the conduit is in the range of 120 to 600° C.

12. The process according to claim 10, wherein the residence time in the conduit is 0.1 to 3 seconds.

13. The process according to claim 10, wherein the quantity of the carotenoid suspension to be transferred is 0.05 to 100 liters/minute.

14. The process according to claim 10, wherein the carotenoid is at least one selected from the group consisting of β-carotene, canthaxanthin, astaxanthin, apocarotenal, citranaxanthin and cryptoxanthin.

15. The process according to claim 10, wherein the particle size of the carotenoid is 50 μm or less.

16. The process according to claim 10, wherein the high boiling organic liquid is a paraffin having 10 to 40 carbon atoms, a terpene compound having 10 to 50 carbon atoms or a fatty acid glyceride having 10 to 80 carbon atoms.

17. The process according to claim 10, wherein the high boiling organic liquid is at least one selected from the group consisting of a fatty acid triglyceride, a fatty acid diglyceride, a fatty acid monoglyceride and an edible oil.

18. The process according to claim 10, wherein an antioxidant is added in preparation of the carotenoid suspension.

19. The process according to claim 10, wherein the content of carotenoid in the carotenoid suspension is 0.5 to 90% by mass based on the whole carotenoid suspension.

20. The process according to claim 10, wherein the emulsifier is a fatty acid ester of ascorbic acid, a sucrose fatty acid ester or a sorbitan fatty acid ester.

21. The process according to claim 10, wherein the temperature at the time of the emulsification is 90° C. or less.

22. A process for producing a carotenoid emulsion which comprises heating a suspension of the carotenoid in a high boiling organic liquid having a boiling point of at least 150° C., by passing the suspension through a conduit of from 0.1 to 50 mm inside diameter heated to a temperature in the range of from 120 to 700° C. for a residence time of 0.05 to 5 seconds or by mixing the suspension with a high boiling organic liquid having a boiling point of at least 150° C. heated to a temperature in the range of 120 to 500° C. for a time of from 0.05 to 10 seconds, to dissolve the carotenoid, and then immediately adding the resulting solution into an aqueous solution of an emulsifier to emulsify the solution, wherein the dissolution of carotenoid by heating is carried out by mixing the carotenoid suspension with the heated high boiling organic liquid.

23. The process according to claim 22, wherein the same kind of a high boiling organic liquid as used in preparation of the carotenoid suspension is used as the heated high boiling organic liquid.

24. The process according to claim 22, wherein the temperature of the heated high boiling organic liquid is in the range of 150 to 500° C.

25. The process according to claim 22, wherein the time of the heating by mixing is 0.05 to 5 seconds.

26. The process according to claim 22, wherein the total of the amount of the heated high boiling organic liquid and the amount of the high boiling organic liquid constituting the carotenoid suspension is 1 to 20 times the mass of the carotenoid contained in the carotenoid suspension.

27. The process according to claim 22, wherein the carotenoid is at least one selected from the group consisting of β-carotene, canthaxanthin, astaxanthin, apocarotenal, citranaxanthin and cryptoxanthin.

28. The process according to claim 22, wherein the particle size of the carotenoid is 50 μm or less.

29. The process according to claim 22, wherein the high boiling organic liquid is a paraffin having 10 to 40 carbon atoms, a terpene compound having 10 to 50 carbon atoms or a fatty acid glyceride having 10 to 80 carbon atoms.

30. The process according to claim 22, wherein the high boiling organic liquid is at least one selected from the group consisting of a fatty acid triglyceride, a fatty acid diglyceride, a fatty acid monoglyceride and an edible oil.

31. The process according to claim 22, wherein an antioxidant is added in preparation of the carotenoid suspension.

32. The process according to claim 22, wherein the content of carotenoid in the carotenoid suspension is 0.5 to 90% by mass based on the whole carotenoid suspension.

33. The process according to claim 22, wherein the emulsifier is a fatty acid ester of ascorbic acid, a sucrose fatty acid ester or a sorbitan fatty acid ester.

34. The process according to claim 22, wherein the temperature at the time of the emulsification is 90° C. or less.

* * * * *